US012002147B2

(12) United States Patent
Vetter et al.

(10) Patent No.: US 12,002,147 B2
(45) Date of Patent: Jun. 4, 2024

(54) METHOD AND SYSTEM FOR OPTIMIZING DISTANCE ESTIMATION

(71) Applicant: SIEMENS HEALTHINEERS AG, Forchheim (DE)

(72) Inventors: Christoph Vetter, Hopewell, NJ (US); Kaloian Petkov, Lawrenceville, NJ (US); Rishabh Shah, Wentworth Point (AU); Sandra Sudarsky, Bedminster, NJ (US)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/659,905

(22) Filed: Apr. 20, 2022

(65) Prior Publication Data

US 2022/0343586 A1    Oct. 27, 2022

(30) Foreign Application Priority Data

Apr. 27, 2021    (DE) ...................... 10 2021 110 797.0

(51) Int. Cl.
*G06T 15/08*    (2011.01)
*A61B 34/10*    (2016.01)
(Continued)

(52) U.S. Cl.
CPC .............. *G06T 15/08* (2013.01); *A61B 34/10* (2016.02); *A61B 34/20* (2016.02); *A61B 90/36* (2016.02);
(Continued)

(58) Field of Classification Search
CPC ......... G06T 15/08; G06T 7/11; G06T 7/0012; G06T 15/04; G06T 15/205; G06T 15/50;
(Continued)

(56) References Cited

U.S. PATENT DOCUMENTS

2005/0203380 A1    9/2005  Sauer et al.
2017/0251900 A1*   9/2017  Hansen ................ A61B 1/3132
(Continued)

FOREIGN PATENT DOCUMENTS

EP    3418978 A1    12/2018
EP    3804629 A1 *  4/2021   ............. A61B 34/20

OTHER PUBLICATIONS

Zhang, Mengshi, et al. "Multiple instruments motion trajectory tracking in optical surgical navigation." Optics express 27.11 (2019): 15827-15845. (Year: 2019).*
(Continued)

*Primary Examiner* — Xin Sheng

(57) ABSTRACT

Distance estimation is optimized in virtual or augmented reality. A distance map of a surgical instrument to a region of interest is determined, at least at the beginning and when a position of the surgical instrument has changed. A render-image is rendered based on a medical 3D image and the position of the surgical instrument, at least at the beginning and when the position of the surgical instrument has changed. At least the region of interest and those parts of the surgical instrument positioned in the volume of the render-image are shown in the render-image. Based on the distance map, at least for a predefined area of the region of interest, visible, acoustic, and/or haptic distance-information is added.

17 Claims, 8 Drawing Sheets

(51) Int. Cl.

| | |
|---|---|
| *A61B 34/20* | (2016.01) |
| *A61B 90/00* | (2016.01) |
| *G06T 7/00* | (2017.01) |
| *G06T 7/11* | (2017.01) |
| *G06T 15/04* | (2011.01) |
| *G06T 15/20* | (2011.01) |
| *G06T 15/50* | (2011.01) |
| *G06T 19/00* | (2011.01) |
| *G06T 19/20* | (2011.01) |

(52) U.S. Cl.
CPC .............. *G06T 7/0012* (2013.01); *G06T 7/11* (2017.01); *G06T 15/04* (2013.01); *G06T 15/205* (2013.01); *G06T 15/50* (2013.01); *G06T 19/006* (2013.01); *G06T 19/20* (2013.01); *A61B 2034/107* (2016.02); *A61B 2034/2065* (2016.02); *A61B 2090/365* (2016.02); *G06T 2207/30056* (2013.01); *G06T 2210/41* (2013.01); *G06T 2215/16* (2013.01)

(58) Field of Classification Search
CPC .................. G06T 19/006; G06T 19/20; G06T 2207/30056; G06T 2210/41; G06T 2215/16; A61B 34/10; A61B 34/20; A61B 90/36; A61B 2034/107; A61B 2034/2065; A61B 2090/365
See application file for complete search history.

(56) References Cited

U.S. PATENT DOCUMENTS

| | | | | |
|---|---|---|---|---|
| 2018/0260996 | A1* | 9/2018 | Schneider | G06T 15/08 |
| 2020/0178928 | A1* | 6/2020 | Park | A61B 8/14 |
| 2022/0039773 | A1* | 2/2022 | Mihajlovic | A61B 90/36 |
| 2023/0091099 | A1* | 3/2023 | Wang | A61B 34/20 |

OTHER PUBLICATIONS

A. G. Bruce Gooch, Non-photorealistic rendering, CRC, 2001. Chapter. 10.
A. M. Puerta, "The power of shadows: shadow stereopsis," Journal of the Optical Society of America, vol. 6, No. 2, pp. 309-311, 1989.
Jens Krüger, et al.; "ClearView: An Interactive Context Preserving Hotspot Visualization Technique," IEEE Trans Vis Comput Graph, 2006.
J. T. Kajiya "The rendering equation", ACM SIGGRAP Computer 15 Graphics, 1986.
Kroes T, Post FH, Botha CP (2012) Exposure Render: An Interactive Photo-Realistic Volume Rendering Framework. PLoS One 7(7): e38586.
Krüger J., Westermann R.: Acceleration techniques for GPU-based volume rendering. In Proc. of IEEE Visualization 2003 (2003), pp. 287-292.
Jean-Marc Hasenfratz, et al.; "A survey of Real-Time Soft Shadows Algorithms," Computer Graphics Forum, vol. 22, No. 4, pp. 53-774, 2003.
R. Fernando, "Percentage-closer soft shadows," SIGGRAPH, p. 35, 2005.
S. K. Khuu, J. Gordon, K. Balcomb and J. Kim, "The perception of three-dimensional cast-shadow structure is dependent on visual awareness," Journal of Vision, vol. 14, 2014.
Thomas Kerwin "Enhancements in Volumetric Surgical Simulation", The Ohio State University, 2011, specifically, chapter 5.
Hansen, et al.; Improving Spatial Perception for Medical Augmented Reality with Interactable Depth Layers; Term: Feb. 2016-Jan. 2019; online at http://www.var.ovgu.de/projects.php.
Liktor, et al.; "Stochastic soft shadow mapping." Computer Graphics Forum. vol. 34. No. 4. 2015.
Heinrich, et al.; "Augmented Reality Visualisation Concepts to Support Intraoperative Distance Estimation"; In: 25th ACM Symposium on Virtual Reality Software and Technology; Year: 2019, pp. 1-2.

\* cited by examiner

METHOD AND SYSTEM FOR OPTIMIZING DISTANCE ESTIMATION

RELATED APPLICATION

This application claims the benefit of German Patent Application No. 10 2021 110 797.0, filed Apr. 27, 2021, which is hereby incorporated by reference in its entirety.

FIELD

The present embodiments relate to optimizing distance estimation in virtual or augmented reality. Especially, proximity guidance augmentation for medical procedures and planning with a distance encoded visualization is provided. The present embodiments describe methods to improve the effect of shadows in medical images and add additional visual and non-visual cues for a better depth perception and device navigation in virtual or augmented reality simulations of multi-device surgical interventions. It is also applicable for single device procedures or virtual reality simulations.

BACKGROUND

Depth perception in humans is influenced by many factors like motion parallax, perspective, lighting and shading, stereopsis, or convergence. One important factor for depth perception are shadows (see e.g., A. M. Puerta, "The power of shadows: shadow stereopsis," Journal of the Optical Society of America, vol. 6, no. 2, pp. 309-311, 1989 or S. K. Khuu, J. Gordon, K. Balcomb and J. Kim, "The perception of three-dimensional cast-shadow structure is dependent on visual awareness," Journal of Vision, vol. 14, 2014).

Shadows improve the perception of depth and could therefore be useful for planning purposes, for example guiding an instrument in the rendering of a planning volume.

In the technical field of augmented reality or virtual reality, a physician relies on completely artificial images (virtual reality) or real images that are artificially enhanced (augmented reality), wherein the images are typically provided with additional information. It should be noted that augmented reality and virtual reality is not bound to glasses-like devices. Also, a normal screen like a computer monitor could provide a scene for virtual/augmented reality. For example, a physician may perform an operation in front of a display looking at an image rendered from MRT-data and control a surgical instrument in a patient.

Until now for virtual reality, medical images are typically rendered with photorealistic shadows, allowing a depth impression. Concerning augmented reality, most images already have shadows, since they are images of a real scene. However, accurate lighting and shadows based on real-world light sources may be rendered for virtual objects placed into the real environment, e.g., for simulation.

There are also several information visualization methods that enhance depth navigation that do not rely on shadows.

The most important related research for this invention disclosure is non-photorealistic rendering (see e.g., A. G. Bruce Gooch, "Non-photorealistic rendering", CRC, 2001 or Thomas Kerwin "Enhancements in Volumetric Surgical Simulation, The Ohio State University, 2011, specifically, chapter 5). Non-photorealistic rendering can be used for animation purposes in the entertainment industry.

For the section on trade-offs, research that develops focus and context regions as in the clearView paper (see J. S. R. W. Jens Krüger, "ClearView: An Interactive Context Preserving Hotspot Visualization Technique," IEEE Trans Vis Comput Graph, 2006) are relevant. In this paper, the view is divided into areas of user focus and context regions that differ in the visualization, quantitatively for example by higher resolution or higher graphic fidelity or qualitatively by using different rendering techniques or even non-photorealistic rendering.

However, sometimes the depth perception based on shadows is not enough, especially in the case when other factors like stereopsis are not present, e.g., in the example above, when a procedure is watched on a normal display. Thus, there is the need for enhancing depth perception (with quantifiable distance information) based on shadows.

SUMMARY AND DETAILED DESCRIPTION

It is the object to improve the known systems, devices, and methods to facilitate a better depth perception and especially allow proximity guidance augmentation for medical procedures and planning with a distance encoded visualization.

This object is achieved by a method, a system, a control device, and a medical imaging system.

A method according to an embodiment for optimizing distance estimation in virtual or augmented reality includes the following acts:

a) providing a (especially reconstructed) medical 3D image of a volume (i.e., a volumetric real-world space imaged by a scanner, e.g., a reconstructed anatomical image) including a segmented anatomical object within a region of interest, b) providing 3D information of the position of a surgical instrument, c) determining a distance map of the surgical instrument to the region of interest, at least at the beginning of the method and in the case the position of the surgical instrument has changed, d) rendering a render-image based on the 3D image and the information of the position of a surgical instrument, at least at the beginning of the method and in the case the position of the surgical instrument has changed, wherein at least the region of interest is shown and those parts of the surgical instrument positioned in the volume of the render-image, and wherein based on the distance map, at least for a predefined area of the region of interest (e.g., in the region of a shadow) visible, acoustic, and/or haptic distance-information is added, e) outputting the render-image and repeating at least acts b) to e).

In the following, the acts are further explained. The method according to an embodiment optimizes distance estimation in the rendered 3D image by the added visible, acoustic, and/or haptic distance information, e.g., tinting and/or contour lines based on distance information rather than light propagation.

a) Providing a (Especially Reconstructed) Medical 3D Image of a Volume (e.g., in a Patient) Including a Segmented Anatomical Object within a Region Of Interest.

This medical 3D image together with information about a segmented anatomical object within a region of interest may be downloaded from an archive. However, also 3D data of an image may be reconstructed from raw data, and predefined information is used to select a region of interest. This predefined information may be a given position or may be a special shape determined in the 3D-image.

A 3D image may be acquired from a medical image modality, like e.g., magnetic resonance imaging (MRI), computed tomography (CT), positron emission tomography (PET), single photon emission computed tomography (SPECT), ultrasound, and others. The volumetric image data of the 3D image may represent an anatomical structure of a human or an animal. Other embodiments relate to non-anatomical objects (implants and/or artificial structures) in medical or anatomical volumes or to non-medical use for industrial applications, like failure analysis in e.g., chip technology.

In praxis, a medical scanner may acquire raw data, and reconstruction algorithms are used to obtain a 3D image or a stack of 2D images. During volume rendering, a reconstruction filter can be used to estimate scalar values at arbitrary 3D location, e.g., for volume ray-casting.

Especially during a virtual or real medical procedure, where a sequence of images is recorded during this procedure, the following acts are applied:
  optionally: reconstruct a 3D-image (from recorded data),
  select a predefined region of interest, especially including an organ in the image,
  segmenting an anatomical object in the region of interest (especially the organ).

The 3D images may be images recorded by a medical imaging apparatus, e.g., computed tomography (CT), magnetic resonance imaging (MRI), ultrasound imaging. They can include 3D volumetric data or a stack of 2D images. It is also possible to work with other images that contain depth information, for example photos or videos taken by depth cameras, synthetic images, or images generated from light fields. However, when working with real images, additional acts are preferred, for example the detection of shadows in the input images and possibly the approximation or reconstruction of additional depth values, since only the depth of pixels in direct view of the camera are known. For later preparing the distance map, the depth of every sample within a 3D volume, at least in the region of interest, should be known.

The segmentation can be performed with a segmentation algorithm well known in the art. This may be achieved with or without user input. For the present embodiments, it does not matter how the segmentation is performed. However, the quality of the guidance is of course determined by the quality of the segmentation. Thus, the segmentation should be accurate. For example, where organs are segmented from the medical images, the output of the algorithm could be some sort of a map that describes which points belong to the object. Examples of segmentations can include surface meshes and binary volumes, among others.

A region of interest ("ROI") is a general selection of a space where certain operations are made. Objects of interest for a physician are inside a region of interest. As region of interest, any volume including a structure that a physician might be interested in can be used. A preferred region of interest may e.g., include a medical device (whether a surgical device or an implant like a stent), a simulated device, a pathological structure (e.g., a calcification or lung nodules), or alien matter (whether digested, internal bleeding or external matter from injuries).

b) Providing 3D Information of the Position of a Surgical Instrument.

Since an image is rendered in the course of the method, the expression "surgical instrument" here means information about the shape (i.e., the volume) of this instrument. This may be a shape measured (e.g., in the image) or known (since the used instrument is well known). The word "position" means here the actual spatial coordinate as well as the orientation of the surgical instrument. This means that the expression "the position of a surgical instrument" means the volume in space that is (or should be in a simulation) occupied with the surgical instrument. The method may use information about a real instrument used in an actual medical intervention as well as information about a virtual instrument, e.g., used for training or simulation.

c) Determining a Distance Map of the Surgical Instrument to the Region of Interest (ROI) . . .

With the knowledge of the position of the surgical instrument (see previous act), the distance map can be determined. This distance map (also referred to as "(signed) distance field") are scalar 3D volumes that provide for every voxel in the volume the shortest distance (possibly approximate) to an object in a region of interest, like e.g., a segmented organ. Preferably, the distance map provides for every point in space (or at least the points of the surgical instrument) the distance to the closest voxel that belongs to the object. Distance maps can be computed for any 3D object, including segmented organs and medical device surfaces.

This act is performed at the beginning of the method, since otherwise there would not exist any information for the rendered image, as well as in the case the position of the surgical instrument has changed, since then the image has to change accordingly. The act may be also performed at other occasions, e.g., when the position of artificial lighting has changed or if the position of the camera has changed or if the segmentation in the region of interest has changed. The act is preferably also performed in the case where the ROI or an organ in the ROI moves, e.g., due to bowel movement, breathing or heartbeat. Alternatively, some form of uncertainty visualization can provide an indication that the visualization is not exact. The act could also be repeated after a predefined time interval; however it should be noted that every new determination needs computing time. Thus, in this act, the distance of the surgical instrument to the ROI is encoded into a distance map that is updated every time the surgical instrument is moved.

It should be noted that the expression "has changed" means a change beyond a predefined spatial threshold. Infinitesimal changes may not be regarded, since they "cost" computing power without any serious advantage. It should also be noted that it is state of the art to determine the position of a surgical instrument. The position of the instrument may e.g., be measured by tracking, e.g., optical tracking, magnetic tracking, or easily detected in the image data of the 3D image.

d) Rendering a Render-Image . . .

The general techniques of rendering are well known in the art. Calculating a visualization (rendering) is typically performed by executing at least one rendering algorithm. Rendering may use any volume rendering technique, but high-performance ones may be preferable to maintain interactivity, such as interactive volume raycasting. For more details for the interactive volume raycasting it is referred to KRUGER J., WESTERMANN R.: Acceleration techniques for GPU-based volume rendering. In Proc. of IEEE Visualization 2003 (2003), pp. 287-292. Final rendering may use the same or a different volume rendering algorithm that provide more realistic rendering, e.g., Monte Carlo volumetric path tracing, see e.g., Kroes T, Post F H, Botha C P (2012) Exposure Render: An Interactive Photo-Realistic Volume Rendering Framework. PLoS ONE 7(7): e38586.

In other embodiments, volume raycasting with raytraced shadows, deep shadow maps, ambient occlusions, and/or other global illumination effects, e.g., single- or multiple-scattering approximations, reflsysections, color bleeding are used.

Methods and systems for segmented volume rendering is e.g., explained in US 2018/260996 A1, where a special method is shown to composite three-dimensional (3D) digital volumetric data onto a two-dimensional (2D) image. In the art, the quality and appearance of the resulting image can vary widely from one volume rendering engine to another due to the choice of different tradeoffs in different implementations.

A preferred method for cinematic rendering is shown in document EP 3 418 978 A1. For visualizing an inhomogeneous three-dimensional object, which is represented by volume data, a large number of light rays are simulated for a respective image pixel, which light rays are associated with the image pixel. The volume data here indicates a density of the object to be imaged in an object volume. The density can here be in particular a physical density, an optical density, a refractive index, and/or a brightness value, color value, transparency value, and/or opacity value and be given in scalar, vectorial, or tensorial form. The image pixels can be arranged, in particular, virtually on an imaging plane or a curved imaging surface. According to embodiments, for a respective light ray that enters the object volume, i) a scatter position is determined in dependence on the density along the visual ray, ii) a scatter direction is selected in dependence on a random process, and iii) the visual ray is scattered at the scatter position in the selected scatter direction. The random process can here be based, for example, on a pseudorandom or quasi-random number generator. Acts i) to iii) are repeated until the light ray is absorbed in the object volume or exits the object volume, wherein the exiting visual ray is incident on an illumination source, and an illumination contribution of the light ray to the respective image pixel is ascertained in dependence on a brightness and/or color value of the illumination source. A statistical average is taken over the respective illumination contributions of the large number of visual rays in order to ascertain a brightness and/or color value for the associated image pixel.

The goal of a renderer is to solve the Rendering Equation (J. T. Kajiya "The rendering equation", ACM SIGGRAP Computer Graphics, 1986) by integrating over all light paths in the scene. In practice, a renderer may use Monte Carlo integration (e.g., unbiased volumetric path tracing), or solve a simpler version of the integral (e.g., no scattering/shadows such as in volume raycasting). Specifically, in Monte Carlo path tracing, interaction events between the light ray and the inhomogeneous media are computed using a stochastic process. Diffuse or specular reflections and transmission preferably handle the case where the optical opacity gradient magnitude is large enough so that the interaction event is handled as an implicit surface scattering event. If the gradient magnitude is low, the scattering is preferably described by a phase function, e.g., Henyey-Greenstein Phase Function. In typical scattering scenarios, the scattered light ray is either absorbed, or eventually hits a light source (inside or outside of the volume), in which case it contributes to the illumination at the visualization pixel. A shading model describes how the interaction event modifies the color of the ray, e.g., the surface color is multiplied into the ray color for diffuse reflections, emissive color is added, etc. In one example for a renderer with image-based lighting, the light probe describes an infinitely far away light source. In general, there may be light sources interior and exterior to the volume, e.g., described as surfaces, as in Kroes et al. In the context of one embodiment, the shadows are preferably created by physical (e.g., spherical) or non-physical (e.g., adapted per surface) localized light sources.

The rendering is based on the 3D image and the information of the position of a surgical instrument, since this is the relevant data: an observer should see the relative position of the surgical instrument to segmented objects in the medical image within the region of interest.

The rendering must be performed at least at the beginning of the method and in the case the position of the surgical instrument has changed (the position of the instrument is very important for an operation).

Again, similar to the determination of the distance map, this act is performed at the beginning of the method (to have a render-image at the start) as well as in the case the position of the surgical instrument has changed, since then the render-image has to change accordingly. The act may be also performed at other occasions, e.g., when the position of artificial lighting has changed (since in this case shadows will change, too), if the position of the camera has changed, or if the segmentation in the region of interest has changed. The act is preferably also performed in the case the ROI or an organ in the ROI moves, e.g., due to bowel movement, breathing, or heartbeat. Alternatively, some form of uncertainty visualization can provide an indication that the visualization is not exact. The act could also be repeated after a predefined time interval. However, it should be noted that every new determination needs computing time.

It is preferred that the rendering will be performed every time, the distance-map has changed, the volume has been changed, a visibility map has changed (see below), or the position of the virtual camera has changed.

The method could also be performed by always rendering an image, e.g., every ¹⁄₂₅ s. However, depending on the complexity of the rendering, that frame rate might not be achievable, and it wastes computing power. Changes are preferably accumulated until the next rendering act is performed since a tracker has usually a much higher update frequency than is feasible for the rendering.

This rendering act includes some sub acts referring to selecting a part of the image and adding visible and/or acoustic and/or haptic distance information.

selecting a part of the image. In this act, at least the region of interest is selected to be shown. Additionally, those parts of the surgical instrument are selected that are positioned in the selected volume of the render-image. It should be noted that the render-image does not have necessarily to show the whole 3D-image as provided. It could also show only a part of the initial 3D-image where the region of interest, e.g., including an organ, is positioned. If the surgical instrument is near enough to be present in the selected volume, it is shown, if it is outside the volume, it is not shown. However, even in this case, its shadow will preferably be calculated to provide an impression, where the surgical instrument is. There could be included a marker pointing in the direction of the surgical instrument in the case it is outside the rendered volume. The selection itself is made in an automatic manner, e.g., based on preferences and/or the position of the region of interest.

optional: shadowing. In this preferred act, the shadow of the surgical instrument is calculated (and preferably visualized in the render-image) at least on the region of interest. When there is more than one surgical instrument, preferably the shadow of every surgical instrument is calculated and preferably also visualized.

Shadowing is state of the art. A preferred standard approach of shadowing is computing shadow rays. However, a preferred technique that is less accurate but faster is shadow mapping. In the case of augmented reality and/or when a real 3D-image with shadows is used, shadows can be recognized by estimating real-world lighting parameters. For example, there has been developed a long list of shadow algorithms for different use cases like real-time or not real-time, soft or hard shadows, rasterization or raytracing. For a survey of real-time oriented soft shadows (for example see M. L. N. H. F. X. S. Jean-Marc Hasenfratz, "A survey of Real-Time Soft Shadows Algorithms," Computer Graphics Forum, vol. 22, no. 4, pp. 53-774, 2003). A fast method for soft shadows for rasterized graphics has been developed in R. Fernando, "Percentage-closer soft shadows," SIGGRAPH, p. 35, 2005. These shadow algorithms can serve as basis for our non-photorealistic shadow algorithms.

It is clear that lighting is essential for rendering and, therefore, a predefined arrangement of artificial light-sources is used for rendering, e.g., a key-light at the right side of the virtual camera. However, suitable lighting techniques are well known in the art.

It should be noted that the method preferably does not add a shadow where there would not be a shadow in a photorealistic image. However, it should be noted that artificial light sources could be used, where the shading is adapted locally near the medical instrument or an optimized virtual light source position can be computed per pixel based on properties of an organ surface near the tip of a device. As shown in the following act, the method modifies the appearance of a shadow, at least in the ROI.

add visible distance information. This is a very important act of the method. At least for a predefined area of the region of interest (preferably in the region of the shadow), a visible distance-information is added based on the distance map. This distance-information is preferably distance-dependent tinting of shadows and/or the addition of distance-dependent contour lines (preferably together with shadows). The preferred tinting or the preferred contour lines may be color-coded, especially, in the case when two or more surgical instruments are used. In that case, the shadow of every surgical instrument another color could be assigned.

Thus, this embodiment goes beyond visual realism by embedding additional information that specifically increases the perception of the proximity between structures, at the cost of the visual realism.

alternatively, or additionally: add acoustic and/or haptic distance information. It is preferred that in addition to visible distance-information or as alternative also non-visual distance-information could be generated, such as sound-information or haptic information. For example, could a haptic data glove provide this haptic information when a user comes near the surgical instrument. Also, an alarm sound could be output if the surgical instrument touches an organ.

Haptics and sound are part of typical AR and VR systems. Given the scene data (e.g., 3D medical images, segmented objects, medical devices, and the distances between them), a generalized rendering process preferably produces a signal that is perceived and processed by the user.

Rendering processes described above produce images with quantifiable distance information encoded in shadows through non-physical alterations. In this preferred enhancement, sonification techniques are applied to the results, and the sound rendering may be modified based on the distance information, e.g., varying the level/frequency of a positional 3D sound as the device moves. The same can be applied to haptic rendering, e.g., modifying the tactile response of a fingertip haptic device in a non-physical way as the distance information changes.

Although the focus is primarily on visual rendering, acoustic, and/or haptic outputs could be alternative or additional embodiments. In a preferred embodiment, the equivalent to visual contour lines in acoustic rendering is a set of directional tones with increasing frequency, played when the distance between a device and organ crosses a set of discrete thresholds. A preferred alternative to color coding shadows based on the device would be modifying the sound level based on distance and the frequency based on the device ID.

Haptic rendering can be implemented similarly. The encoding of the distance information may use different heuristics in each rendering domain.

e) Outputting the Render-Image and Repeating at Least Acts b) to e).

The render-image may be output via special augmented or virtual reality glasses or on a normal display, e.g., a monitor or television.

The method is repeated as long as the user wants, e.g., for the time of an operation or simulation. A repetition should start with the provision (determination) of the position of the surgical instrument (act b), however, it is preferred that it also includes the provision of a (new) medical 3D image (act a), e.g., concerning ultrasound images, where a reconstruction and segmentation could easily be performed on each repetition. However, additional imaging could be performed at each repetition act (not necessarily always in 3D and not necessarily for reconstruction of a 3D image), which could be used to update the rendering and object segmentations.

Due to act d), the outputted render-image may include specially tinted shadows and/or distance-depending contour lines and, thus, non-photorealistic shadow rendering in order to enhance the shadow rendering with additional information. Therefore, instead of solely relying on physically accurate shadows, the method increases the amount of information that can be conveyed with shadows.

This method has the advantage that a surgeon could be guided with the render-images to avoid critical anatomy during interventions, for example a vasculature during a liver ablation. The embodiment achieves this through enhanced proximity perception, the perception of the distance between two objects in the image, by the added visible distance-information. In contrast to exact physical rendering, non-photorealistic rendering according to an embodiment helps to make a proximity guidance quantifiable.

Non-physical light sources allow the placement of a shadow at the point on the surface closest to the device. The shadow softness and color may be set directly based on the distance data, e.g., using a color map/heat map for the shadow color.

In a different embodiment, the direction of motion may also affect the visualization. E.g., a single or multiple aspects may utilize distance along the direction of motion rather than closest distance.

Guidance may be provided by a single or multiple aspects of the rendering (including acoustic and haptic), e.g., modifying shadow hardness along the suggested direction of motion.

One embodiment may use (especially reconstructed) anatomical images, segmented anatomical structures within a region of interest and tracked device data.

A system according to an embodiment for optimizing distance estimation in virtual or augmented reality, preferably for performing a method according to any of the preceding claims, includes the following components:

A data interface designed for receiving a medical 3D image of a volume including a segmented anatomical object within a region of interest, and 3D information of the position of a surgical instrument, a determination unit (processor), designed for determining a distance map of the surgical instrument to the region of interest, at least at the beginning of the method and in the case the position of the surgical instrument has changed, a rendering unit (renderer or graphics processing unit), designed for rendering a render-image based on the 3D image and the information of the position of a surgical instrument, at least at the beginning of the method and in the case the position of the surgical instrument has changed, wherein at least the region of interest is shown, and those parts of the surgical instrument are positioned in the volume of the render-image, and preferably, wherein a shadow of the surgical instrument at least in the region of interest is calculated and visualized, and wherein based on the distance map, at least for a predefined area of the region of interest, visible distance-information is added, the distance-information preferably being distance-depending tinting of shadows and/or preferably distance-depending contour lines, a data interface, designed for outputting the render-image.

A control device (controller) according to an embodiment for controlling a medical imaging system includes a system according to an embodiment. Alternatively, or additionally, it is designed to perform the method according to an embodiment. The control device may include additional units or devices for controlling components of a medical imaging system.

A medical imaging system according to an embodiment, e.g., a MRI, a CT, or, an ultrasound system, includes a control device according to an embodiment.

Some units or modules of the system or the control device mentioned above can be completely or partially realized as software modules running on a processor of a system or a control device. A realization largely in the form of software modules can have the advantage that applications already installed on an existing system can be updated, with relatively little effort, to install and run these units of the present application. The object is also achieved by a computer program product with a computer program that is directly loadable into the memory of a device of a system or a control device of a medical imaging system, and which includes program units (instructions) to perform the acts of the method when the program is executed by the control device or the system. In addition to the computer program, such a computer program product can also include further parts such as documentation and/or additional components, also hardware components such as a hardware key (dongle etc.) to facilitate access to the software.

A non-transitory computer readable medium such as a memory stick, a hard-disk or other transportable or permanently-installed carrier can serve to transport and/or to store the executable parts of the computer program product so that these can be read from a processor unit of a control device or a system. A processor unit can include one or more microprocessors or their equivalents.

Particularly advantageous embodiments and features are given by the dependent claims, as revealed in the following description. Features of different claim categories may be combined as appropriate to give further embodiments not described herein.

According to a preferred method, a 3D image of a volume including a segmented anatomical object within a region of interest is provided by the acts:

optionally: reconstruct a 3D-image, especially a MRI or CT image, wherein the 3D image may be present as a voxel-image or a stack of 2D images resulting in a continuous 3D volume.

select a predefined region of interest, especially including an organ in the image, and segment an anatomical structure (an object) within the region of interest, e.g., an organ.

This preprocessing may e.g., include a segmentation of an organ (e.g., the liver) in a region of interest, in order to only change the shadows cast on the segmented object inside the region of interest. Another possibility is to define the region of interest using an eye tracker on a user, similarly to the idea behind foveated rendering.

According to a preferred method, in the course of rendering a render-image, a shadow of the surgical instrument is calculated. In the case there are two or more surgical instruments, it is preferred that shadows for a number of the surgical instruments are calculated. The calculated shadows are preferably also visualized in the render-image. As already said above, it is well known how to calculate shadows.

According to a preferred method, the distance-information is a distance-depending tinting of shadows, wherein color-tinting (a color is assigned to a shadow) is preferred. In the case there are two or more surgical instruments, it is particularly preferred that different tinting is used for the shadows of different surgical instruments. To enhance the attention of an observer, it is preferred that tinting is only applied in the region of interest and/or on a predefined segmented organ. Otherwise (outside the ROI or on another organ) the shadow is preferably not tinted, but still there. For example, shadows with distance information are rendered only within bounding box around a medical device representation, or within a 10 mm boundary of a segmented object.

Concerning tinting, a fragment of the rendered image could be regarded. Fragments are data structures that correspond to pixels but have additional information beyond color, like depth, opacity, normal information etc. Several fragments are potentially combined to form a final pixel in the image.

For each fragment, it could be determined whether it lies in a shadow or not. In the case, a fragment is in a shadow, it could be tinted according to its distance (the value in the distance map), preferably, only if it is on a segmented organ or inside a region of interest.

The distance dependence of tinting is preferably accomplished in that the color gets brighter or more saturated the closer the instrument is to the segmentation or the region of interest. A color attribute of the shadow could be manipulated in order to indicate the value of the distance. A lookup table of different colors dependent on the distance could also be used.

An important non-photorealistic element of the shadow is the tinting, that is based on distance information rather than light propagation. The same applies to the display of the contour lines. The rendering is not based on actual physical structures even if it looks plausible. Another example would be the mapping of different colors to different distances for the tinting of the shadow. This again would look realistic but is not physically based.

It is alternatively or additionally preferred that in the course of rendering, the distance-information is realized by distance-depending contour lines. These contour lines (or "banding") could be used instead of tinting or additionally, to encode the distance information. The contour lines especially including numerical values of distances, e.g., written besides respective contour lines.

This approach allows a more precise visualization of the distance than simple tinting. Users can also transfer their knowledge of topographic map visualization to this type of visualization. It is preferred that a modulo operator is used on the distance in order to create bands and for the contour lines these bands are compressed into lines, especially anti-aliased. Regarding different surgical instruments, these contour lines preferably have different colors, or different line-styles for different surgical instruments. The modulo operator does determine the distance between the contours. It can be constant or varying. It is preferred that the distance is smaller the smaller the distance of the surgical instrument to the ROI is.

This tinting and these contour lines are non-photorealistic shadow rendering features that enhance the shadow rendering with additional information.

For encoding distance information into the shadow by tinting the shadow color, information is needed, where the surgical instrument is located and where the shadow lies. The distance of the instrument is encoded in the distance map. The information on whether something is shadowed by the instrument can be performed by either computing shadow rays or by performing a lookup into a shallow stochastic visibility map.

According to a preferred method, a (shallow) stochastic visibility map is computed. A (shallow) stochastic visibility map is a two-dimensional map that indicates whether position A is visible from position B. This map can be computed for example by computing a shadow map. Unless the shadow map belongs to a point light source however, the shadow map does not convey exact shadowing information. For area light-sources, several views can be computed and averaged in order to give a probability of visibility or an approximate percentage of occlusion.

As an alternative to a stochastic visibility map, shadow rays could be computed. Shadow rays may be the preferred approach when non-physical light sources are used and this procedure could be combined with the shadow mapping for the physical sources in the scene. However, visibility maps are a compromise between accuracy (approximate) and speed (fast). For a higher accuracy at slightly lower speed a deep shadow map can also be used. Shadow rays have a higher accuracy but also a higher cost in terms of speed, so depending on the requirements there are several methods that are state of the art.

The stochastic visibility map is preferably updated (computed again) in the case that the view on the rendered image (i.e., the position of a virtual camera characterizing the view on the rendering-image) has been changed, e.g., by input of a user. It should be noted that a change of view does not change the relative position of instrument and organ (and thus not the distance map), but the angle of view on this system.

Preferably, the visibility map is updated in the case additional artificial light sources are used or the position of a light-source has been changed.

In the case an organ in the region of interest moves, it is also preferred to update the stochastic visibility map.

As already indicated above, it is preferred that in the case that the position of more than one surgical instrument is provided to the method, in course of the rendering, the visible distance-information is visualized differently for different surgical instruments. For different surgical instruments, different colors, textures, and/or line-styles are preferably used.

In a scenario of a surgery with multiple instruments are used or simulated, the depth information between the different surgical instruments could be disambiguate by this special encoding. For example, different tinting colors could be used for different instruments, so that it becomes clear which instrument is associated with which shadow. Also, the banded or contour line depiction of shadows can be extended with different colors for these bands and possibly combined with transparency. Especially in the umbra of several instruments, this makes it clear which shadow is cast by which instrument.

The encoding could also be realized by tinting the shadow of one group of instruments and using contour lines for a second group of instruments.

Advantageously, this clearly displays the distances of the different instruments without guesswork which distance to which instrument is visualized.

According to a preferred method, based on the position of a surgical instrument, an additional artificial light-source is positioned behind the surgical instrument. This means that the surgical instrument is positioned between the light-source and the ROI. The light-source is oriented such that it shines on the region of interest. Thus, a shadow of this surgical instrument is produced that is clearly visible on the region of interest. This is advantageous to disambiguate multiple instruments more easily and to make sure that a shadow is visible at the correct spot. The additional artificial light-source is preferably placed behind the surgical instrument along the vector from the point to the end of the device. This ensures a shadow in the direction where the tip of the surgical device is moving.

In order to speed up the effects discussed above, the methods can be accelerated at the cost of slightly lower visual quality in the following ways. The more expensive path tracing for accurate shadows as well as correct ambient lighting can be restricted to regions of interest, whether they are defined by segmented organs, distance maps of surgical instruments or the penumbra or umbra regions provided by shadow mapping.

Shadow computation could be restricted according to the visibility map or the region of interest. During rendering, for each computation it could be checked whether the interaction point lies within the region of interest. If it is outside, it could be reverted to less expensive shadow computation for example using shadow maps or possibly no shadow computation at all. Whenever a light interaction within the region of interest is computed, more expensive shadow computation methods are chosen, whether adding ambient occlusion or a higher number of shadow rays. This way, the expensive and accurate shadow computations are only performed in the regions of interest. The same can be done for ambient lighting or ambient occlusion effects. They are preferably only performed within a region of interest.

Shadow maps are a fast but reasonably high-quality method of computing shadows, with methods like percentage-closer soft shadows (see e.g., R. Fernando, "Percentage-closer soft shadows," SIGGRAPH, p. 35, 2005) even producing soft shadows. Instead of using the shadow maps directly for shadow computations, this method preferably uses the "cheap" shadow map lookup to determine the course of the shadow computation. The shadow map is preferably used as a first act towards determining which shadow algorithm should be used where in the visualization.

If ambient lighting is desired in order to more clearly show the regions within the shadow, instead of using expensive ray tracing a non-physical light source is preferably added under the instrument that only illuminates the region in the shadow cast by the instrument. This again, can be determined by a lookup into the visibility map or by computing shadow rays.

In order to speed up the computation of the visibility map, the visibility computation can be restricted to mesh-to-mesh visibility, so that only the mesh of the instrument and the mesh of the segmentation is taken into account while the volume itself is ignored. Another option to accelerate the visibility is using ray casting instead of path tracing to generate the visibility map.

The method may also include elements of "cloud computing". In the technical field of "cloud computing", an IT infrastructure is provided over a data-network, e.g., a storage space or processing power and/or application software. The communication between the user and the "cloud" is achieved by means of data interfaces and/or data transmission protocols.

In the context of "cloud computing", in a preferred embodiment of the method, provision of data via a data channel (for example a data-network) to a "cloud" takes place. This "cloud" includes a (remote) computing system, e.g., a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system, the abovementioned units are present on the "cloud" side. A preferred system further includes, a local computing unit connected to the system via a data channel (e.g., a data-network, particularly configured as RIS or PACS). The local computing unit includes at least one data receiving interface to receive data. Moreover, it is preferred if the local computer additionally has a transmission interface in order to send data to the system.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION

Figure 1:
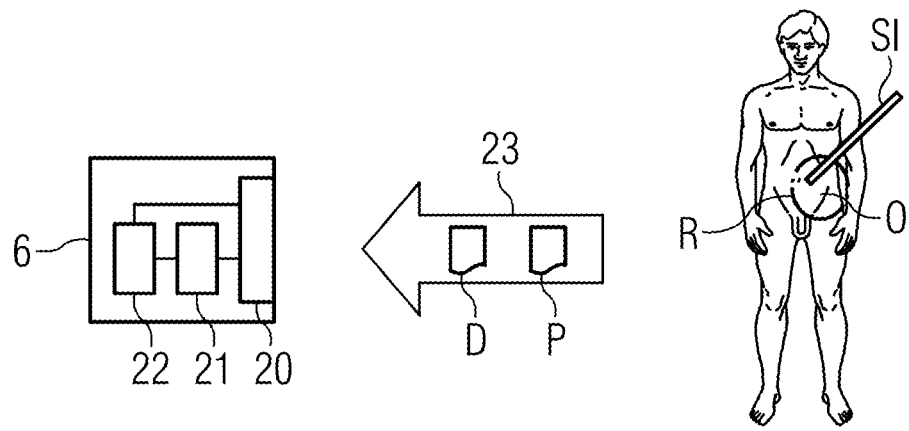
FIG. 1 shows an example of a system according to an embodiment.
Figure 3:
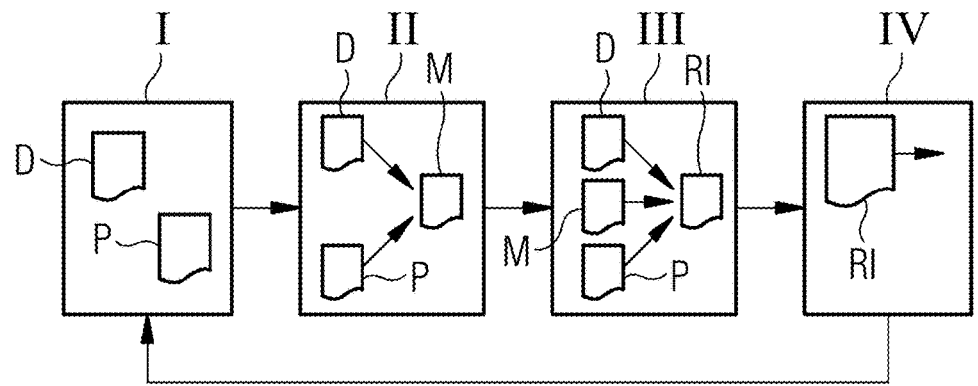
FIG. 3 shows a block diagram of the process flow of a preferred method according to an embodiment.
Figure 4:
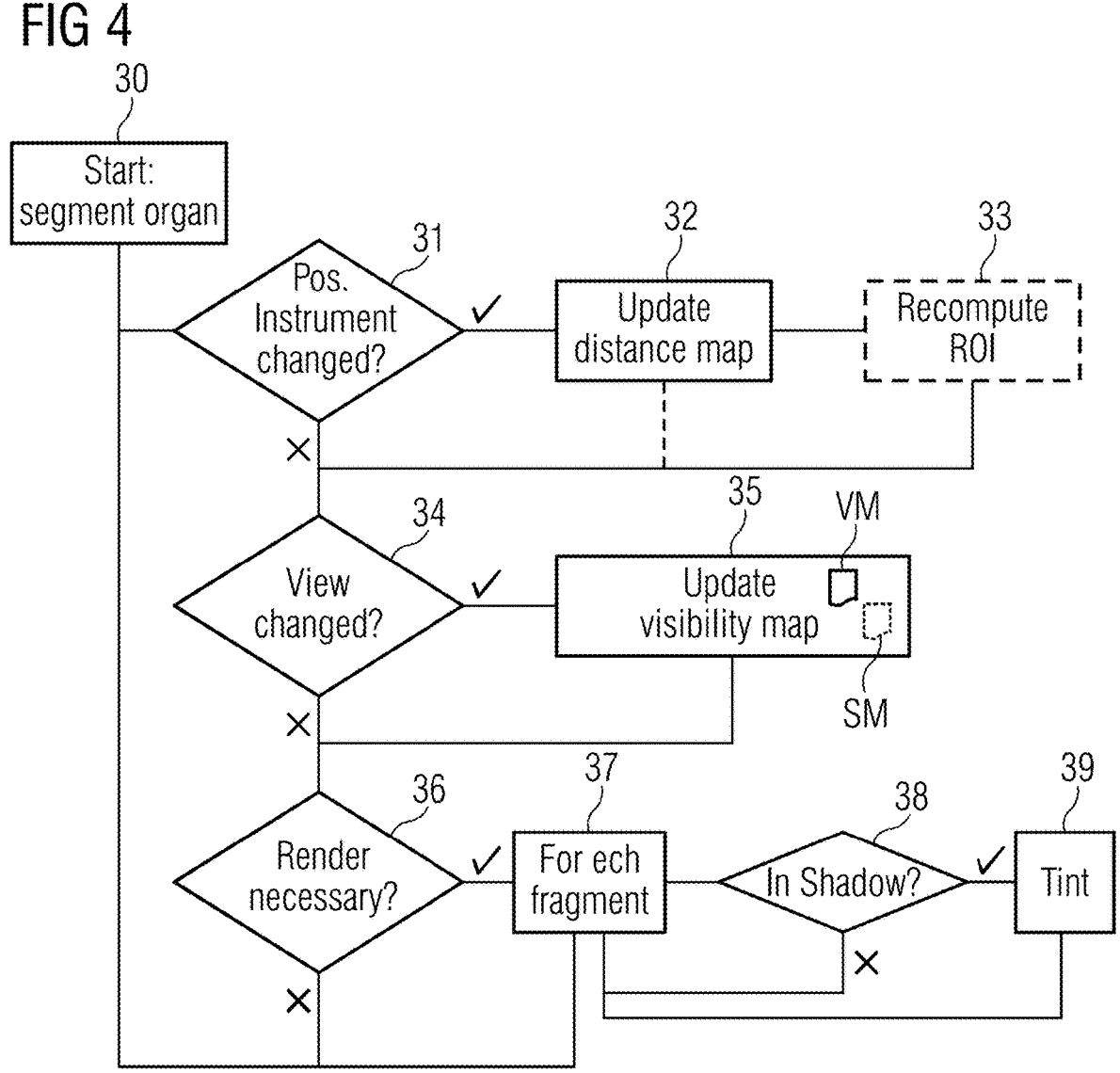
FIG. 4 shows a block diagram of the process flow of a preferred special method according to an embodiment.

FIG. 1 shows an example of a system 6 for optimizing distance estimation in virtual or augmented reality, designed to perform the method according to an embodiment (see FIGS. 3 and 4). The system 6 includes data interface 20, a determination unit 21 and a rendering unit 22. The data interface 20 receives a medical 3D image D of a volume including a segmented anatomical object O within a region of interest R, and 3D information of the position P of a surgical instrument SI. In this example, the surgical instrument SI could be an endoscope in the patient.

It should be noted that the scene could be a scene of an operation with a real patient and a real surgical instrument SI. However, the invention is also applicable for simulations of an operation, with a virtual avatar of a patient or images of a real patient and a virtual representation of the surgical instrument SI.

The determination unit 21 determines a distance map M of the surgical instrument SI to the region of interest R, at least at the beginning of the method and in the case the position P of the surgical instrument SI has changed (see e.g., FIGS. 3 and 4 referring to the method).

The rendering unit 22 renders a render-image RI based on the 3D image D and the information of the position P of a surgical instrument SI, at least at the beginning of the method and in the case the position of the surgical instrument SI has changed, wherein at least the region of interest R is shown and those parts of the surgical instrument SI positioned in the volume of the render-image RI, and wherein based on the distance map M, at least for a predefined area of the region of interest R, visible distance-information in form of tinting T or contour lines C is added.

In this example, the data could be provided e.g., via a data network 23, e.g., PACS (Picture Archiving and Communication System) to the data interface 20 that could also be used for outputting the render-image RI.

Figure 2:
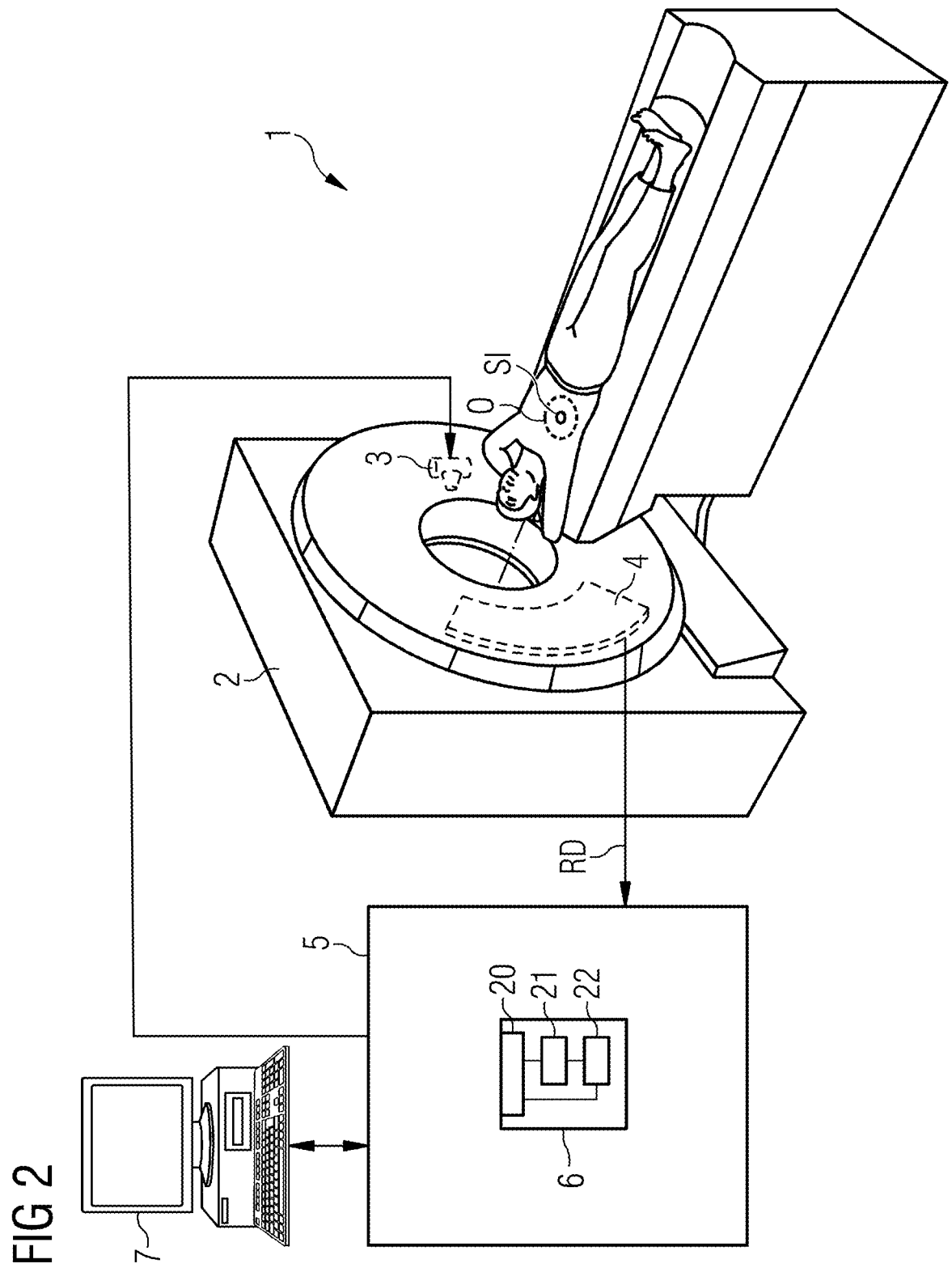
FIG. 2 shows a simplified CT system with a system according to an embodiment.

FIG. 2 shows a simplified computer tomography system 1 with a control device 5 including a system 6 for optimizing distance estimation in virtual or augmented reality, designed to perform the method according to an embodiment (see FIGS. 3 and 4). The computer tomography system 1 has in the usual way a scanner 2 with a gantry, in which an x-ray source 3 with a detector 4 rotates around a patient and records raw data RD that is later reconstructed to images by the control device 5.

An object O in the patient is indicated that could e.g., be the liver (see following figures). It could also be understood as a region of interest R (see also following figures). In the object O, there is indicated a surgical instrument SI. In difference to FIG. 1, the surgical instrument is shown here in the patient to indicate that the surgical instrument could be completely inside the body (e.g., like a stent or a robot).

It is pointed out that the exemplary embodiment according to this figure is only an example of an imaging system and the invention can also be used on theoretically any imaging system that is used in medical and non-medical environment, e.g., for medical imaging systems such as ultrasound systems or magnetic imaging systems to provide images. It should be noted that the embodiment as described can be used for surgical planning as well as in an interventional setting. In the case of an interventional setting, the typical modality that is used is either CT (as shown) or Xray.

In this figure, only those components are shown that are essential for explaining the embodiment. In principle, such imaging systems and associated control devices are known to the person skilled in the art and therefore do not need to be explained in detail.

The imaging system (here the CT system 1) records images that can be used for the system 6 according to an embodiment, and images of the imaging system are processed by the system 6 according to an embodiment.

A user can interact with the computer tomography system 1 by using terminal 7 that is able to communicate with the control device 5. This terminal 7 can also be used to examine results of the system 6 according to an embodiment or to provide data for this system 6.

The system 6 includes the following components:

A data interface 20 designed to receive a reconstructed medical 3D image D of a volume including a segmented anatomical object O within a region of interest R, and 3D information of the position P of a surgical instrument SI.

A determination unit 21 designed for determining a distance map M of the surgical instrument SI to the region of interest R, at least at the beginning of the method and in the case the position P of the surgical instrument SI has changed.

A rendering unit 22, designed for rendering a render-image RI based on the reconstructed 3D image D and the information of the position P of a surgical instrument SI, at least at the beginning of the method and in the case the position of the surgical instrument SI has changed, wherein at least the region of interest R is shown and those parts of the surgical instrument SI positioned in the volume of the render-image RI, and wherein based on the distance map M, at least for a predefined area of the region of interest, visible distance-information T, C is added.

The shown data interface 20 is in this example also designed for outputting the render-image RI.

The components of the system preferably are software modules.

FIG. 3 shows a block diagram of the process flow of a preferred method for optimizing distance estimation in virtual or augmented reality according to an embodiment.

In act I, a (especially reconstructed) medical 3D image D of a patient O a volume of this patient O) is provided. This 3D image D includes a segmented anatomical object O within a region of interest R (see e.g., following figures).

Also in act I, 3D information of the position P of a surgical instrument SI is provided.

In act II, a distance map M of the surgical instrument SI to the region of interest R is determined. This is done at the beginning of the method and in the case the position P of the surgical instrument SI has changed. Other, where the distance map is updated may also exist.

In act III, a render-image RI is rendered based on the 3D image D and the information of the position P of a surgical instrument SI. In this example, rendering may be performed every time anything in the scene has changed. In the course of rendering, the region of interest R is shown and those parts of the surgical instrument SI positioned in the volume of the render-image RI (see e.g., following figures). Based on the distance map M, for the region of interest, visible distance-information in form of tinting T or contour lines C is added (see following figures).

In act IV, the render-image RI is outputted and acts I to IV are repeated.

Thus, the method uses non-photorealistic shadow rendering methods in order to enhance the shadow rendering with additional information. One preferred approach to encode distance information into the shadow is tinting the shadow color according to the distance from the surgical instrument SI. For this the information on where the surgical instrument SI is located is used and the information where the shadow S lies. The distance of the surgical instrument SI is then encoded into a distance map M that should be updated every time the surgical instrument SI is moved. The information on whether something is shadowed by the surgical instrument SI can be performed by either computing shadow rays or by performing a lookup into a shallow stochastic visibility map VM.

FIG. 4 shows a block diagram of the process flow of a preferred special method according to an embodiment.

At the box "start" 30, the algorithm starts. If the process flow returns to start, it is repeated until a user stops the procedure. At the start, the image can be preprocessed. This preprocessing could be repeated anytime the routine returns to start, but it also could be performed at the beginning, only. The preprocessing here includes a segmentation of an organ O (e.g., the liver shown in the following figures) or a region of interest R, in order to only change the shadow S on the segmentation or inside the region of interest. Another possibility is to define the region of interest R using an eye tracker similarly to the idea behind foveated rendering.

After that, it is examined 31, whether the position of the surgical instrument SI has changed. If yes, the distance map M is updated 32 and preferably (dashed box) the region of interest R is recomputed 33 according to the position of the surgical instrument SI and the segmented organ O. If the optional act is not performed, the procedure follows the dashed line. In the case, the examination is negative (no movement of the surgical instrument SI), the procedure advances without updating/recomputing.

Then, whether the view has changed is examined 34. If yes, the stochastic visibility map VM is updated 35. If the examination 34 is negative (no change of view), the procedure advances without updating. A (shallow) stochastic visibility map VM is a two-dimensional map that indicates whether a position A is visible from a position B. This visibility map VM can be computed for example by computing a shadow map SM. Unless the shadow map SM belongs to a point light source however, the shadow map SM does not convey exact shadowing information. For area light sources, several views can be computed and averaged in order to give a probability of visibility or an approximate percentage of occlusion.

After that, it is examined 36, whether rendering is necessary. If yes, the same loop 37 is then performed for each fragment. In the loop 37, it is examined 38 whether the fragment is in the shadow S or not. If yes, the fragment is tinted 39, if not there is no tinting. The tinting 39 can be performed according to the distance (e.g., the nearer the brighter the color). It could be distinguished whether the fragment is on the segmented organ (tinting) or not (no tinting). It could also be distinguished whether the fragment is inside the region of interest (tinting) or not (no tinting).

Instead of tinting, also contour lines C (see FIGS. 11 to 17) or a banding could be used for distance encoding. This approach allows a more precise visualization of the distance than simple tinting. Users can also transfer their knowledge of topographic map visualization to this new visualization.

Using a distance map M and a (shallow) stochastic visibility map VM as explained above, this method is different only at the level of the actual fragment shading. Preferably, instead of tinting 39 the shadow S with a color, a modulo operator is used on the distance in order to create bands. For the contour lines C, these bands are compressed into lines, possibly anti-aliased.

The algorithm could easily be altered in the loop, by including contour lines C instead of tinting 39 or in addition to tinting 39. For each fragment it is examined whether it is in the shadow S or not. If yes, a modulo operator could be applied as described above, and contour lines C could be drawn according to the distance. It is preferred to show single line bands of the contour lines.

Regarding coloring (in the course of tinting 39 or of colored contour lines C), it is preferred to disambiguate between shadows S by different instruments. In a scenario where surgery with multiple instruments is simulated or performed, it is preferred to disambiguate the depth information between the different surgical instruments SI. This can be achieved by using different approaches or colors for different surgical instruments SI. For example, one surgical instrument SI could be indicated by tinting 39 its color and another with contour lines C. However, both surgical instruments SI could also be disambiguated by tinting 39 or contour lines C having different colors. By associating different tinting colors with different surgical instruments SI, it becomes clear which surgical instrument SI is associated with which shadow S. Also, the banded or contour line C depiction of shadows S can be extended with different colors for these bands and possibly combined with transparency, especially in the umbra of several surgical instruments SI. This makes it clear which shadow S is cast by which surgical instrument SI. More importantly, this clearly displays the distances of the different surgical instruments SI without guesswork which distance to which surgical instruments SI is visualized.

In order to disambiguate more easily and to make sure that a shadow S is visible at the correct spot, an additional artificial light source can be placed behind a surgical instrument SI, along the vector from the point to the end of the device. This ensures a shadow S in the direction where the tip of the surgical instrument SI is moving.

In order to speed up the effects discussed above, the methods can be accelerated at the cost of slightly lower visual quality in the following ways. The more expensive path tracing for accurate shadows S as well as correct ambient lighting can be restricted to regions of interest R, whether they are defined by segmented organs O, distance maps M of surgical instruments SI or the penumbra or umbra regions provided by shadow mapping.

Shadow computation can be restricted according to the visibility map VM or region of interest R. During rendering, for each computation we check whether the interaction point lies within the region of interest R. If it is outside, it could be reverted to less expensive shadow computation for example using shadow maps SM or possibly no shadow computation at all. Whenever a light interaction within the region of interest R is computed, more expensive shadow computation methods are preferably chosen, whether adding ambient occlusion or a higher number of shadow rays. This way, the expensive and accurate shadow computations are only performed in the regions of interest R. The same can be done for ambient lighting or ambient occlusion effects. They are only performed within a region of interest R.

Shadow maps SM are a fast but reasonably high-quality method of computing shadows S, with methods like percentage-closer soft shadows S even producing soft shadows S. Instead of using the shadow maps SM directly for shadow computations, this method preferably uses the cheap shadow map SM lookup to determine the course of the shadow computation. The shadow map SM is then used as a first act towards determining which shadow algorithm is used where in the visualization.

If ambient lighting is desired in order to more clearly show the regions within the shadow S, instead of using expensive ray tracing, a non-physical light source can be added under the instrument that only illuminates the region in the shadow S cast by the surgical instrument SI. This again, can be determined by a lookup into the visibility map VM or by computing shadow rays.

In order to speed up the computation of the visibility map VM, the visibility computation can be restricted to mesh-to-mesh visibility, so that only the mesh of the instrument and the mesh of the segmentation is taken into account while the volume itself is ignored. Another option to accelerate the visibility is using ray casting instead of path tracing to generate the visibility map VM.

Figure 5:
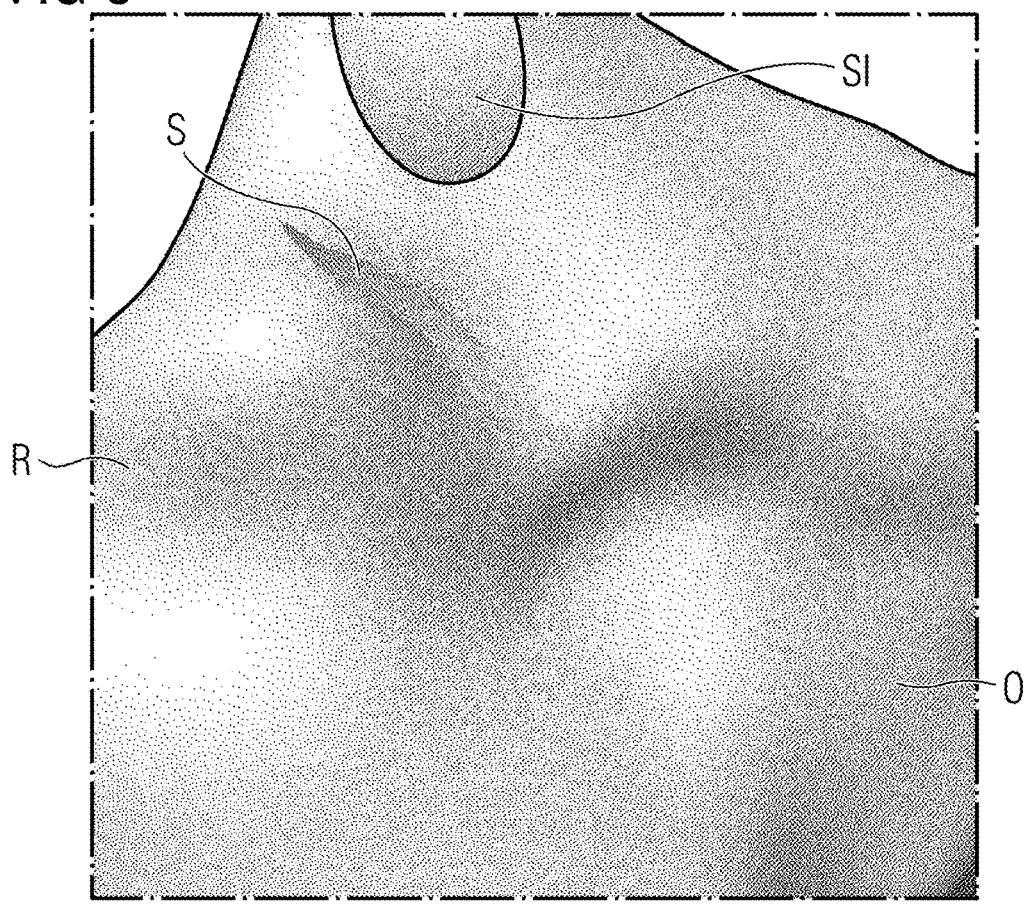
FIG. 5 shows an example scene with a region of interest and a surgical instrument with photorealistic shadows according to the state of the art.
Figure 6:
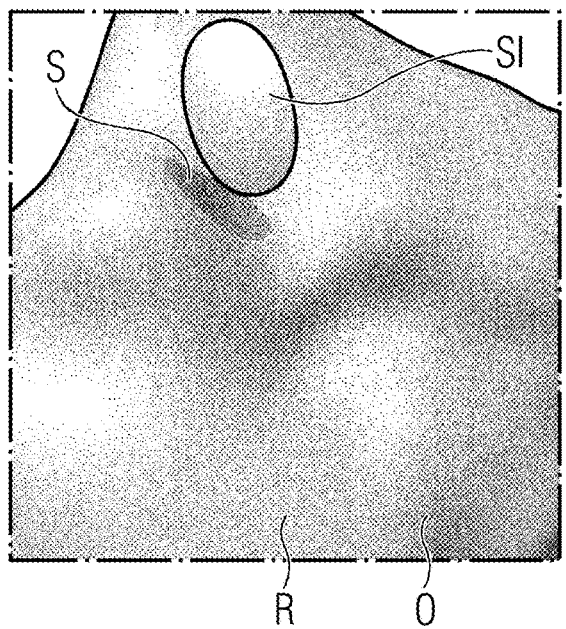
FIG. 6 shows another example scene with a region of interest and a surgical instrument with photorealistic shadows according to the state of the art.
Figure 7:
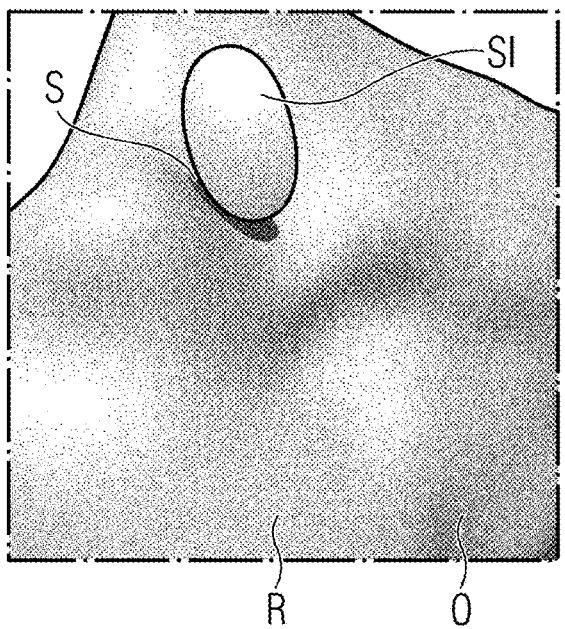
FIG. 7 shows another example scene with a region of interest and a surgical instrument with photorealistic shadows according to the state of the art.

FIGS. 5, 6, and 7 show a scene with a region of interest R and a surgical instrument SI with photorealistic shadows S according to the state of the art. In these figures and in the following figures, the region of interest shows a part of the liver. Thus, here the region of interest (the volume) represents the anatomical object O, i.e., the segmentation O. Here, it is shown a shape (representing a surgical instrument SI) getting closer to a segmented object O (the liver) with a shadow S. The shadow color gets stronger, the closer the shape gets.

In FIG. 5, the surgical instrument SI is relatively far from the region of interest R and its shadow S is relatively faint.

In FIG. 6, the surgical instrument SI is nearer to the region of interest R and its shadow S is more definitive.

In FIG. 7, the surgical instrument SI is relatively near, nearly touching the region of interest R and its shadow S is strong.

Figure 8:
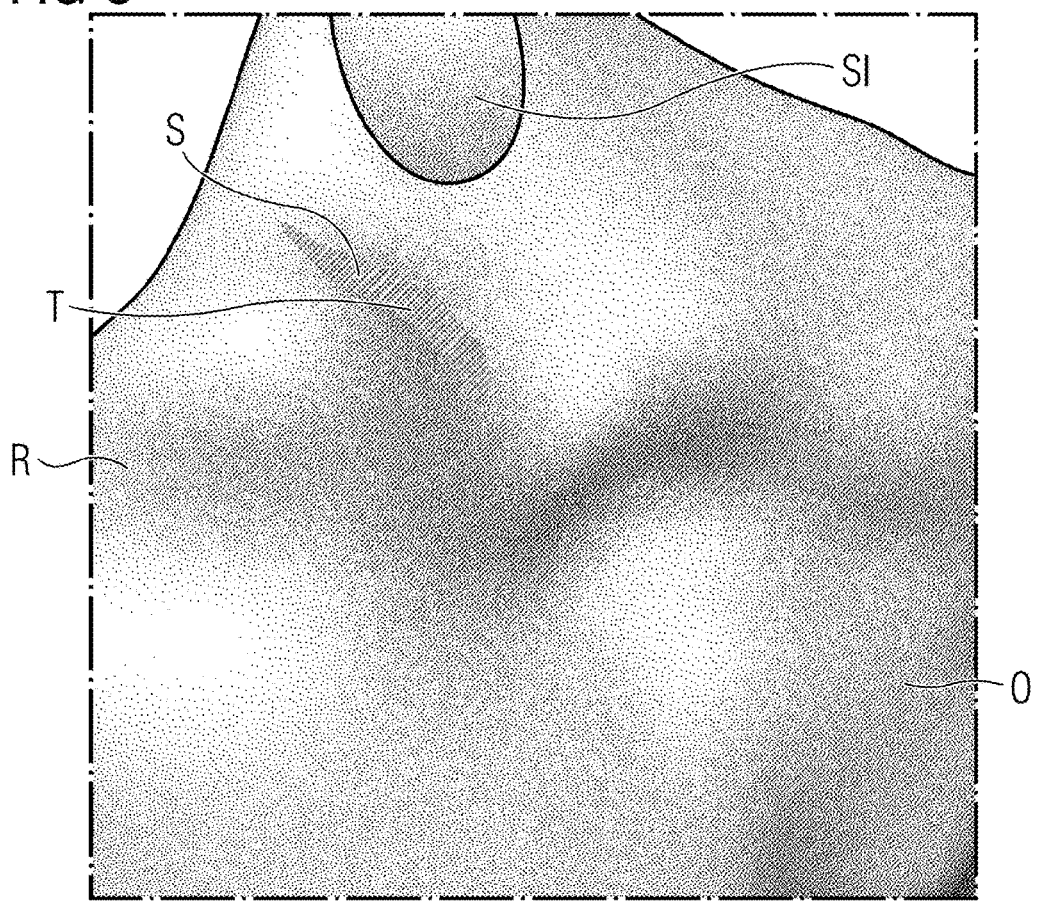
FIG. 8 shows an example scene with a region of interest and a surgical instrument with non-photorealistic tinted shadows.
Figure 9:
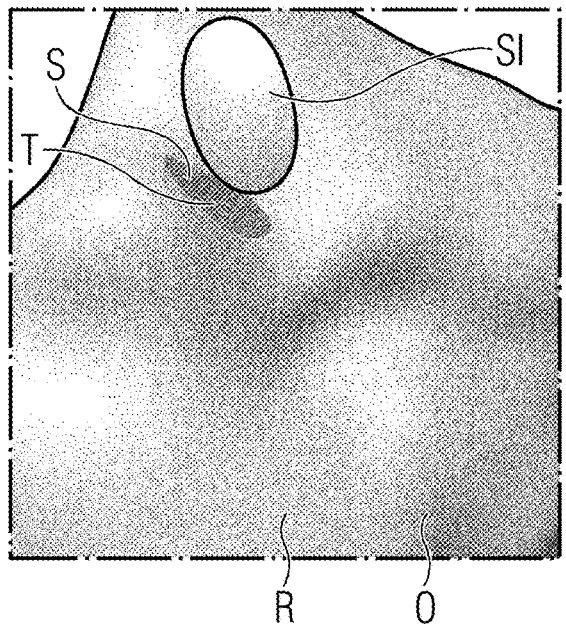
FIG. 9 shows another example scene with a region of interest and a surgical instrument with non-photorealistic tinted shadows.
Figure 10:
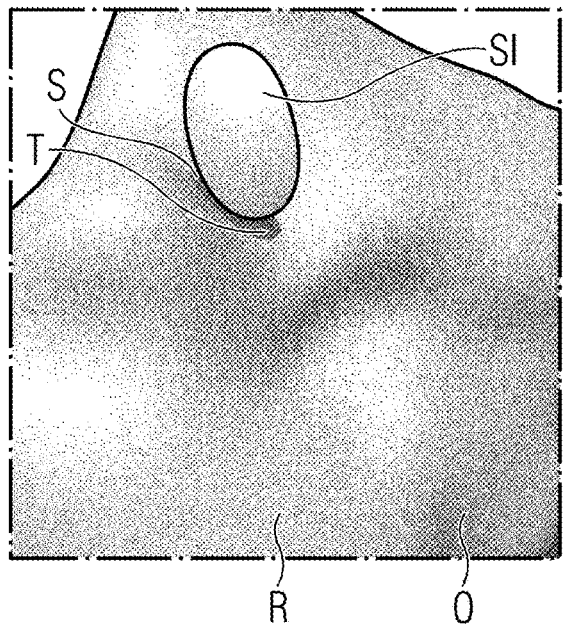
FIG. 10 shows another example scene with a region of interest and a surgical instrument with non-photorealistic tinted shadows.

FIGS. 8, 9 and 10 show a scene similar to FIGS. 5 to 7 with a tinting T added to the shadows S in the region of interest R. It is shown as a shape (again representing a surgical instrument SI) getting closer to a segmented object O (again the liver) with a shadow S tinted in a color, e.g., in red. The shadow color and the tinting gets stronger, the closer the shape gets.

Figure 11:
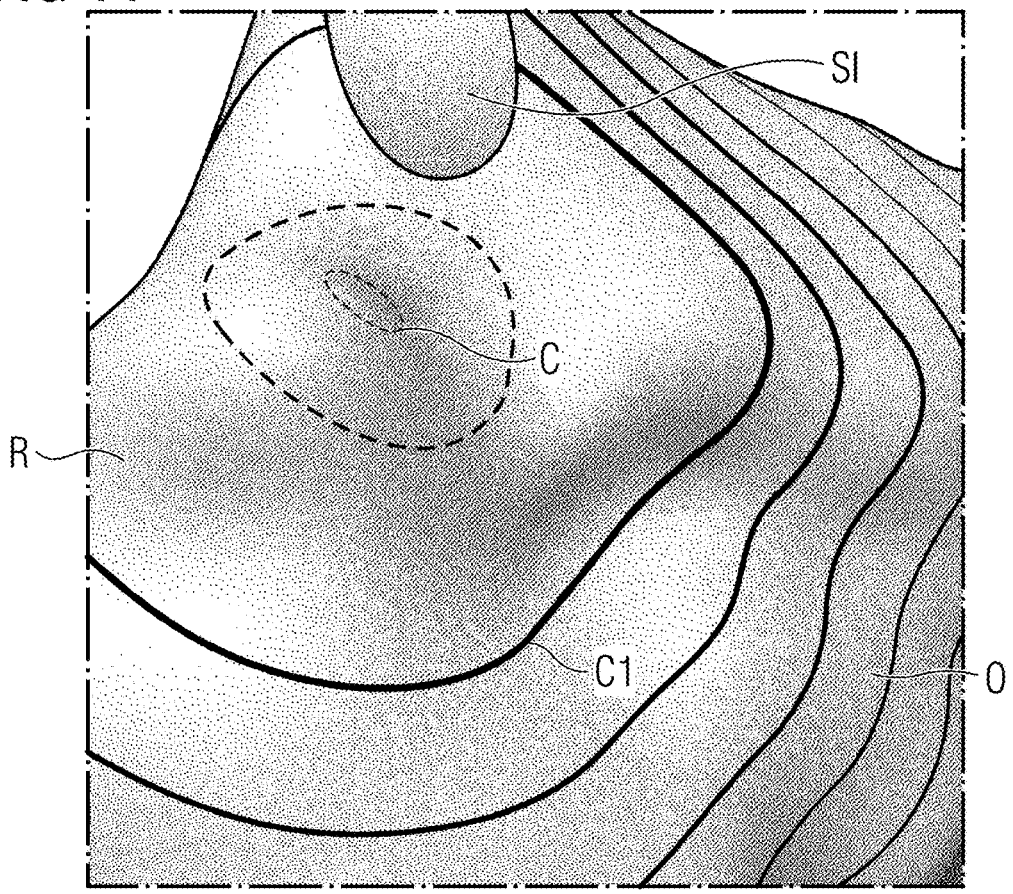
FIG. 11 shows an example scene with a surgical instrument and a region of interest with contour lines.
Figure 12:
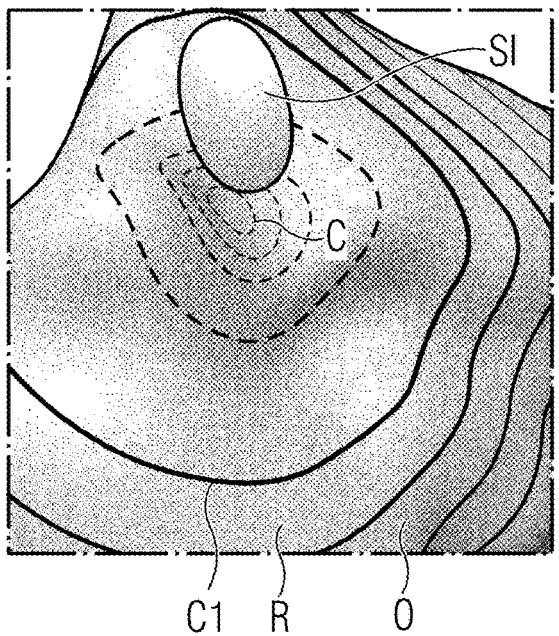
FIG. 12 shows another example scene with a surgical instrument and a region of interest with contour lines.
Figure 13:
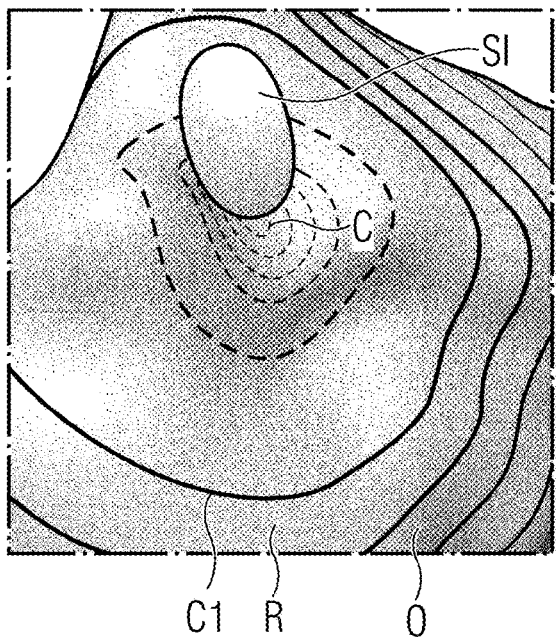
FIG. 13 shows another example scene with a surgical instrument and a region of interest with contour lines.

FIGS. 11, 12 and 13 show a scene similar to FIGS. 5 to 7 with contour lines C instead of shadows S in the region of interest R. The contour lines C are used to indicate the distance of the surgical instrument SI to the object O. There are more dashed contour lines C when the surgical instrument SI is closer. There are two types of contour lines C, C1, one type of contour lines C (dashed) represents the distance of the surgical instrument SI, and the other type of contour line C1 (solid) represents the shape of the object O and is not aligned with the distance of the surgical instrument SI. Here contour lines C replace the shadow S.

Figure 14:
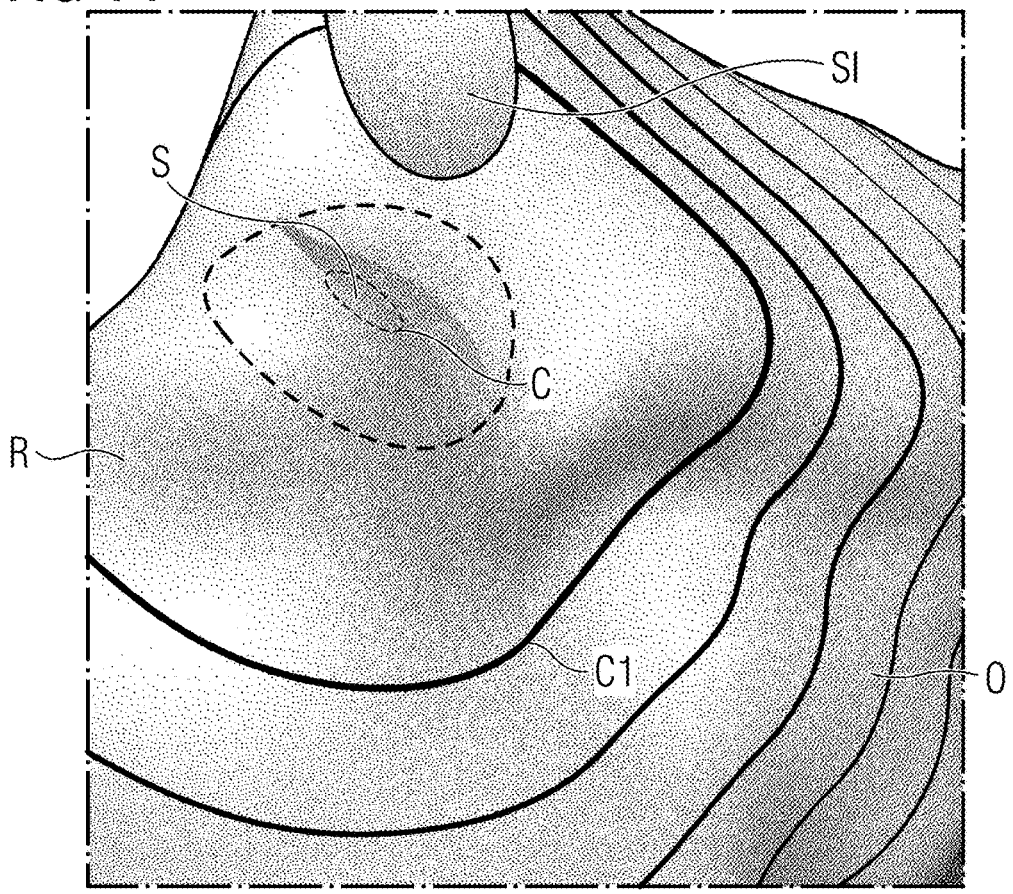
FIG. 14 shows an example scene with a surgical instrument and a region of interest with contour lines and photorealistic shadows.
Figure 15:
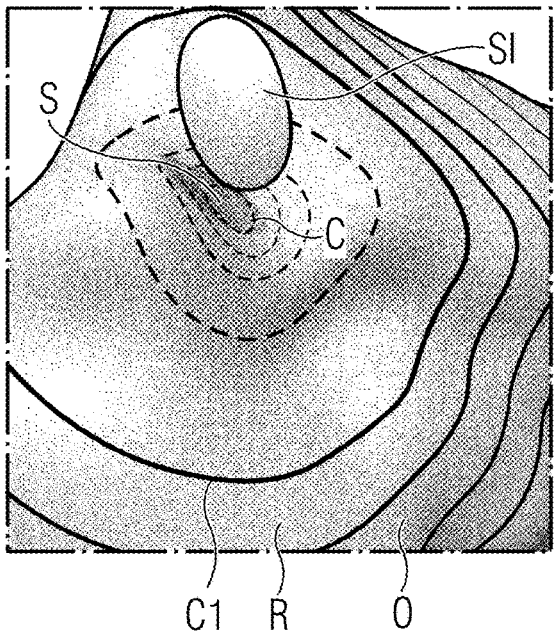
FIG. 15 shows another example scene with a surgical instrument and a region of interest with contour lines and photorealistic shadows.
Figure 16:
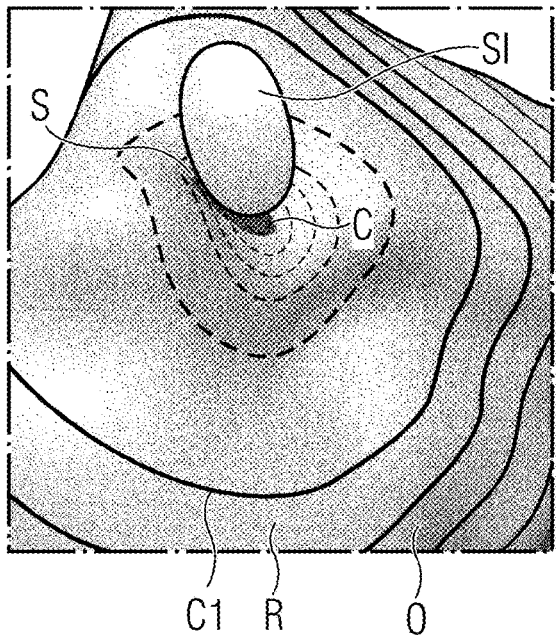
FIG. 16 shows another example scene with a surgical instrument and a region of interest with contour lines and photorealistic shadows.

FIGS. 14, 15 and 16 show the scene from FIGS. 11 to 13 with additional photorealistic shadows S. In these images, the contour lines C are, thus, used in addition to the shadow S to indicate distance between the surgical instrument SI and the segmented object O.

Figure 17:
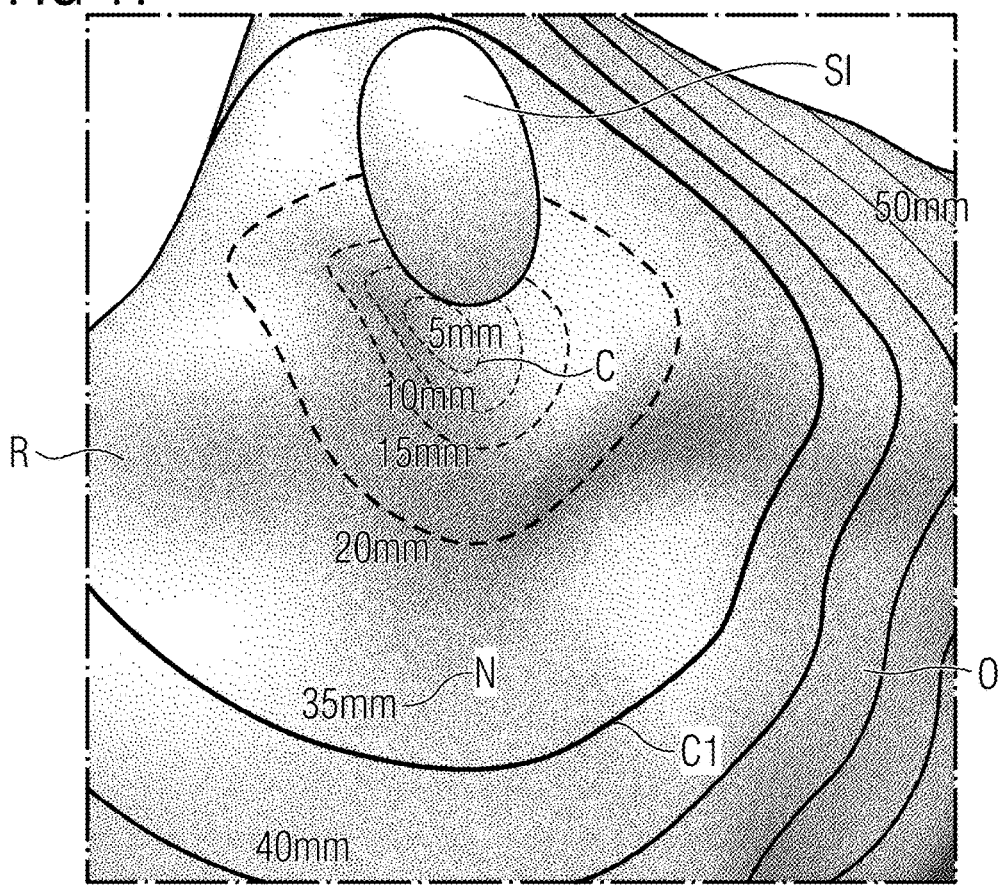
FIG. 17 shows an example scene with a surgical instrument and a region of interest with contour lines and numerical values.

FIG. 17 shows a scene similar to FIG. 11 with contour lines C and numerical values N shown besides the respective contour lines C. Thus, in this image the contour lines C are enhanced with text that indicates the distance in mm.

Figure 18:
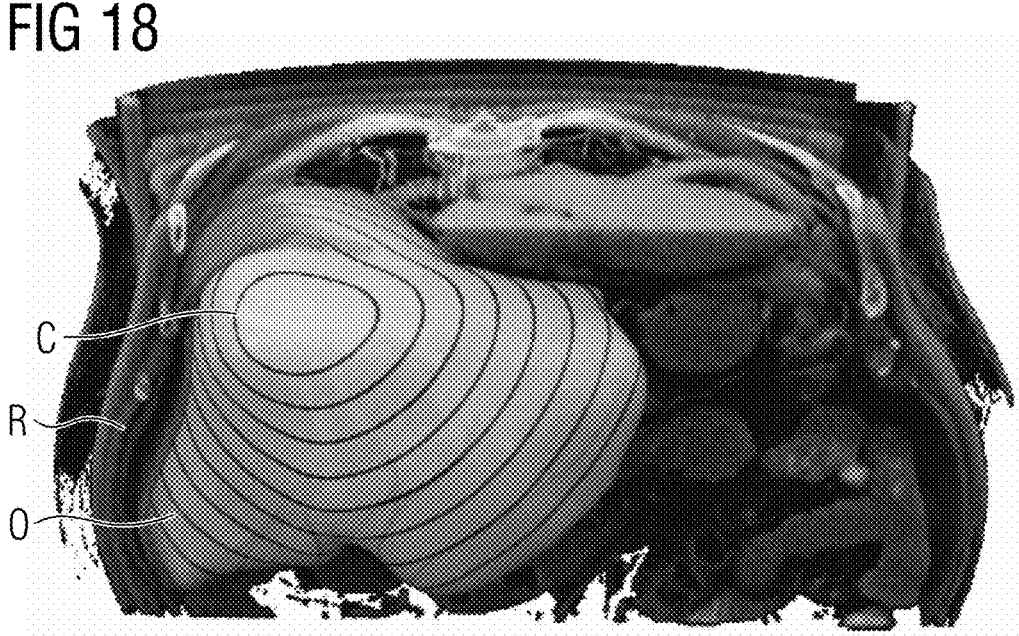
FIG. 18 shows an example region of interest of the human body with contour lines.

FIG. 18 shows a region of interest R of the human body with contour lines C rendered on the liver (the object O in the region of interest R). Such special rendering can be easily implemented for virtual reality simulators or any other sort of rendering. In the case of augmented reality views, the real-world objects would have to be stitched together from additional camera views though.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other acts or elements. The mention of a "unit" or a "device" does not preclude the use of more than one unit or device.

The invention claimed is:

1. A method for optimizing distance estimation in virtual or augmented reality, the method comprising:
   a) providing a medical three-dimensional (3D) image of a volume comprising a segmented anatomical object within a region of interest,
   b) providing 3D information of a position of a surgical instrument,
   c) determining a distance map of the surgical instrument to the region of interest, at least at a beginning of the method and in the case the position of the surgical instrument has changed, the distance map comprising a field of distances from multiple locations of the region of interest to the surgical instrument at a given time,
   d) rendering a render-image based on the 3D image and the information of the position of a surgical instrument, at least at the beginning of the method and in the case the position of the surgical instrument has changed,
   wherein at least the region of interest is shown and those parts of the surgical instrument positioned in a volume of the render-image, and
   wherein based on the distance map, at least for a predefined area of the region of interest, visible, acoustic, and/or haptic distance-information is added to the render-image, the render-image having the visible, acoustic, and/or haptic distance-information that varies by position based on the field of distances,
   e) outputting the render-image and repeating at least acts b) to e).

2. The method according to claim 1, wherein the 3D medical image of the volume comprising is provided by:
   select the region of interest as a predefined region of interest comprising an organ in the 3D medical image, and
   segmenting an anatomical structure within the region of interest.

3. The method according to claim 1, wherein in a course of rendering the render-image, a shadow of the surgical instrument is calculated or shadows for a number of the surgical instruments are calculated.

4. The method according to claim 3, wherein the distance-information is distance-depending tinting of shadows.

5. The method according to claim 4, wherein different tinting is used for the shadows of different surgical instruments, and wherein tinting is only applied in the region of interest and/or on a predefined segmented organ.

6. The method according to claim 1, wherein the distance-information is distance-depending contour lines.

7. The method according to claim 6, wherein the distance information further comprises numerical values (NV) of distances, wherein a modulo operator is used on the distance in order to create bands and for the contour lines, these bands are compressed into anti-aliased lines.

8. The method according to claim 1, wherein the position of more than one surgical instrument is provided and, in course of the rendering, the visible distance-information is visualized differently for different surgical instruments, wherein for the different surgical instruments different colors, textures, and/or line-styles are used.

9. The method according to claim 1, wherein a stochastic visibility map is computed as the distance map.

10. The method according to claim 9, wherein the stochastic visibility map is updated in the case that a view on the rendering-image has been changed, a number of artificial light-sources has been changed, and/or a position of an artificial light-source has been changed.

11. The method according to claim 1, wherein, based on the position of a surgical instrument, an additional artificial light-source is positioned behind the surgical instrument and shining on the region of interest.

12. The method according to claim 1, wherein in determining the distance map of the surgical instrument to the region of interest, the region of interest is recomputed according to the position of the surgical instrument.

13. The method according to claim 12, wherein the region of interest is recomputed according to the position of the surgical instrument and a position of the segmented anatomical object in the region of interest.

14. The method according to claim 1, wherein path tracing or shadow mapping for shadows or for ambient lighting, and/or a computation of the visibility map are restricted to the region of interest.

15. The method according to claim 14, wherein the path tracing or shadow mapping and/or computation of the visibility map are restricted to mesh-to-mesh visibility so that only a mesh of the surgical instrument and a mesh of the segmentation is taken into account while the volume itself is ignored.

16. A system for optimizing distance estimation in virtual or augmented reality, the system comprising:
- a first data interface configured to receive a medical three-dimensional (3D) image of a volume comprising a segmented anatomical object within a region of interest, and to receive 3D information of a position of a surgical instrument,
- a processor configured to determine a distance map of the surgical instrument to the region of interest, the distance map comprising a field of distances from multiple locations of the region of interest to the surgical instrument at a given time,
- a renderer configured to render a render-image based on the 3D image and the 3D information of the position of the surgical instrument, wherein at least the region of interest and those parts of the surgical instrument positioned in a volume of the render-image are shown in the render-image, and wherein, based on the distance map, at least for a predefined area of the region of interest, visible, acoustic, haptic distance-information is added, the render-image having the visible, acoustic, and/or haptic distance-information that varies by position based on the field of distances,
- a second data interface configured to output the render-image.

17. A non-transitory computer-readable medium on which is stored programming that can be read and executed by a computer to optimize distance estimation in virtual or augmented reality, the programming including instructions to:
a) determine a distance map of a surgical instrument to a region of interest, at least at a beginning of the virtual or augmented reality and in the case the position of the surgical instrument has changed, the distance map comprising a field of distances from multiple locations of the region of interest to the surgical instrument at a given time,
b) render a render-image based on a 3D image and a position of a surgical instrument, at least at the beginning and in the case the position of the surgical instrument has changed, wherein at least the region of interest and parts of the surgical instrument positioned in a volume of the render-image are shown, and wherein, based on the distance map, at least for a predefined area of the region of interest, visible, acoustic, and/or haptic distance-information is added, the render-image having the visible, acoustic, and/or haptic distance-information that varies by position based on the field of distances,
c) output the render-image, and
d) repeating acts a) to c).

* * * * *